United States Patent [19]

Kato et al.

[11] Patent Number: 4,675,183

[45] Date of Patent: Jun. 23, 1987

[54] METHOD FOR SOLUBILIZATION OF INTERFERON

[75] Inventors: Yasuki Kato, Shizuoka; Eiji Hayakawa, Susono; Kunitoshi Furuya, Mishima; Akira Kondo, Numazu, all of Japan

[73] Assignee: Kwoya Hakko Kogyo Co., Ltd., Tokyo, Japan

[21] Appl. No.: 726,971

[22] Filed: Apr. 25, 1985

[30] Foreign Application Priority Data

Apr. 28, 1984 [JP] Japan ................... 59-86972

[51] Int. Cl.⁴ .............................. A61K 45/02
[52] U.S. Cl. ......................... 424/85; 435/811
[58] Field of Search .............. 424/85; 435/811; 268/112.5 R; 260/112 R; 530/351

[56] References Cited

U.S. PATENT DOCUMENTS 4,465,622 8/1984 Nobuhara et al. ................ 260/112

FOREIGN PATENT DOCUMENTS 82481 6/1983 European Pat. Off. .
181223 10/1984 Japan .
181224 10/1984 Japan .

*Primary Examiner*—Blondel Hazel
*Attorney, Agent, or Firm*—Antonelli, Terry & Wands

[57] ABSTRACT

A method for increasing the solubility of interferon in water involves admixing an amino acid selected from the group consisting of arginine, histidine, lysine, hydroxylysine, ornithine, glutamine, γ-aminobutyric acid, ε-aminocaproic acid and a salt thereof with interferon.

7 Claims, No Drawings

METHOD FOR SOLUBILIZATION OF INTERFERON

BACKGROUND OF THE INVENTION

The present invention relates to a method for effecting solubilization of interferon in water and an interferon-containing composition which is easily soluble in water.

Interferon is a physiologically active substance expected to be useful as a therapeutic agent because of its biological activities such as antivirus, anti-cancer and like activities. Interferon is classified into type α, type β, type γ, etc., according to the physiological and physicochemical properties, and the origin. Heretofore, interferon has been produced by incubating cells of animals, in particular, cells of humans. However, since the supply of such cells was limited, there has been developed a process for producing interferon which comprises cloning an interferon gene by recombinant DNA technology, introducing it into a microorganism; e.g., *E. coli*, and incubating the microorganism.

Interferon is only slightly soluble in water so that it is difficult to isolate and purify from the culture. Thus, a procedure for solubilizing interferon has been sought.

For the purification of interferon-β, a method using blue Sepharose column is known. In this method, interferon is solubilized using ethylene glycol in an eluate [Jankowski, W. J., et al, Biochemistry, 15, 5182 (1976), Knight, E., Jr., Science, 207, 525 (1980)], but adequate results from this method have not been obtained yet.

Furthermore, Japanese Published Unexamined Patent Application No. 102519/1980 discloses that aromatic amino acids such as tryptophan, phenylalanine, tyrosine, etc., are effective for stabilizing interferon.

However, aromatic amino acids are not readily soluble in water and, therefore, are undesirable as reagents for solubilizing interferon.

SUMMARY OF THE INVENTION

The present invention provides a method for increasing the solubility of interferon in water using an amino acid selected from the group consisting of arginine, histidine, lysine, hydroxylysine, ornithine, glutamine, γ-aminobutyric acid, ε-aminocaproic acid, and a salt thereof such as hydrochloride, sulfate, acetate, glutamate, aspartate and maleate.

DESCRIPTION OF THE INVENTION

Examples of interferon include natural interferon, interferon produced by incubation of animal cells, interferon produced by incubation of a microorganism obtained by recombinant DNA technology, etc. Also included are interferons of any of types α, β and γ. In the present invention, in particular, an excellent effect may be expected with interferon-γ (hereinafter referred to as G-γ-IFN) obtained by recombinant DNA technology.

As the amino acids, arginine, histidine, lysine, hydroxylysine, ornithine, glutamine, γ-aminobutyric acid, ε-aminocaproic acid, a salt thereof, etc., can be used. In particular, arginine, histidine, lysine, hydroxylysine and ornithine have been found to provide a remarkable solubilizing effect.

The effect of solubilizing interferon is exhibited by adding $5 \times 10^{-6}$ mole to $5 \times 10^{-3}$ mole of the amino acid per 1,000,000 units of interferon. The effect is especially remarkable with the addition of the amino acid in an amount of $2.5 \times 10^{-5}$ mole to $2 \times 10^{-3}$ mole.

When the amino acids are used in combination with serum albumin; inorganic salts such as sodium chloride, potassium chloride, sodium carbonate, sodium bicarbonate, potassium phosphate, potassium phosphate monobasic, potassium phosphate dibasic, potassium phosphate tribasic, sodium phosphate, sodium phosphate monobasic, sodium phosphate dibasic, sodium phosphate tribasic, sodium tetraborate and potassium tetraborate; polysaccharides such as chondroitin sulfate, sodium carboxymethylcellulose, dextran, dextrin, cyclodextrin, methylcellulose and ethylhydroxycellulose; surfactants such as benzalkonium chloride, benzethonium chloride, sodium lauryl sulfate, Tween 80, Tween 60, Span 60, Span 40 and Span 20; chelating agents such as edetate disodium, citric acid and glycine, etc., the effect can be markedly increased. Generally the amount of such other additive will vary from $1 \times 10^{-8}$ mole to $1 \times 10^{-2}$ mole per 1,000,000 units of interferon depending on the specific additive selected.

The conventional, freeze-dried, serum albumin-added G-γ-IFN gives white insoluble matters in a solution at 25° C. six hours after it is dissolved in water. However, when G-γ-IFN is dissolved using a 3% (W/V) amino acid solution, insoluble matter is not formed at 25° C. even after six hours.

Further, when freeze-dried G-γ-IFN to which an albumin and an amino acid are added is dissolved in water, insoluble matter is not formed at 25° C. even after six hours.

The present invention also provides an interferon-containing composition containing an amino acid as a solubilizing agent.

The amounts of interferon, the amino acids and the inorganic salts in the composition are the same as in the aforesaid method for solubilization.

Such compositions may incorporate pharmaceutically acceptable preservatives, stabilizers, excipients, binding agents, disintegrating agents, wetting agents, lubricants, coloring agents, aromatic agents, flavoring agents, coating agents, suspending agents, emulsifiers, dissolution aids, buffers, isotonic agents, plasticizers, plastic surfactants, etc.

Examples of the present invention are given hereinafter:

EXAMPLE 1

Preparation of a sample:

In this example, 5 mg of serum albumin and $3 \times 10^6$ units of G-γ-IFN which was prepared by the method described in Reference Example below (hereinafter the same method of preparation shall apply) were dissolved in 2 ml of distilled water and the solution was freeze-dried.

Measurement of Insoluble Matter:

The amount of the insoluble matters in a reconstructed solution of the freeze-dried G-γ-IFN was determined by measuring the absorbance at 400 nm.

The reconstruction was carried out using 5 ml of the amino acid solution shown in Table 1 and an equal amount of distilled water was used as a control. After reconstruction, the solution was stored for six hours at 25° C. and then the solution was put in a 1 cm quartz cell, where the absorbance was measured at 400 nm.

The results of different solutions are shown in Table 1.

TABLE 1

| Amino acid solution | Concentration (W/V %) | O.D. 400 nm at 25° C., 6 hours after |
|---|---|---|
| Distilled water (control) | | 0.260 |
| Arginine monohydrochloride | 3 | 0.026 |
| Lysine monohydrochloride | 3 | 0.045 |
| Histidine | 3 | 0.034 |
| Hydroxylysine | 3 | 0.043 |
| Glutamine | 3 | 0.063 |
| Ornithine acetate | 3 | 0.042 |
| γ-Aminobutyric acid | 3 | 0.077 |
| ε-Aminocaproic acid | 3 | 0.071 |
| Propylene glycol | 5 | 0.231 |

EXAMPLE 2

In this example, 5 mg of serum albumin, 50 mg of an amino acid shown in Table 2 and $3 \times 10^6$ units of G-γ-IFN were dissolved in 2 ml of distilled water, and the solution was freeze-dried.

The freeze-dried product was dissolved in 5 ml of distilled water. The solution was stored for six hours at 25° C., and then the absorbance of the solution was measured at 400 nm.

The results of different amino acids are shown in Table 2.

TABLE 2

| Amino Acid | O.D. 400 nm |
|---|---|
| None | 0.255 |
| Arginine monohydrochloride | 0.029 |
| Lysine monohydrochloride | 0.042 |
| Histidine | 0.028 |
| Ornithine acetate | 0.034 |

EXAMPLE 3

The freeze-dried G-γ-IFN was dissolved in a manner similar to Example 1 except that the concentrations of the amino acids in the solution were changed. The solution was stored for six hours at 25° C., and then the absorbance of the solution was measured at 400 nm.

The results are shown in Table 3.

TABLE 3

| Amino Acid | Concentration (W/V %) | O.D. 400 nm |
|---|---|---|
| Distilled water (control) | | 0.259 |
| Arginine monohydrochloride | 4 | 0.026 |
| Arginine monohydrochloride | 1 | 0.047 |
| Arginine monohydrochloride | 0.5 | 0.093 |
| Lysine monohydrochloride | 1 | 0.061 |
| Histidine | 1 | 0.045 |
| Orinithine acetate | 1 | 0.080 |

EXAMPLE 4

In this example, 5 mg of serum albumin and $3 \times 10^6$ units of G-γ-IFN were dissolved in 2 ml of distilled water, and the solution was freeze-dried. The freeze-dried product was dissolved in 5 ml each of distilled water, a solution of albumin, and a solution mixture of albumin and an amino acid. The solution was stored for six hours at 25° C., and then the absorbance of the solution was measured at 400 nm. The results are shown in Table 4.

TABLE 4

| Solution | O.D. 400 nm |
|---|---|
| Distilled water | 0.256 |
| Solution of serum albumin (4 mg/ml) | 0.208 |
| Serum albumin (4 mg/ml), arginine monohydrochloride (3 w/v %) | 0.025 |

EXAMPLE 5

In this example, 5 mg of serum albumin, 5 mg of sodium chloride and 30 mg of arginine monohydrochloride were added to $3 \times 10^6$ units of G-γ-IFN. The solution was made up to 2 ml with distilled water and put in a vial, followed by freeze-drying.

The freeze-dried product was dissolved in 5 ml of distilled water. The solution was stored for six hours at 25° C., and then the absorbance of the solution was measured at 400 nm. The O.D. value was 0.025. The amount of the G-γ-IFN which remained in the solution after six hours was 98% of the expected value ($3 \times 10^6$ units).

REFERENCE EXAMPLE

Production of interferon-γ with *Escherichia coli* IG-KA-2:

*Escherichia coli* IGKA-2 (FERM BP-496) having recombinant plasmid pGKA-2 was cultivated at 37° C. for 18 hours in LG medium prepared by dissolving 10 g of tryptophan, 5 g of yeast extract, 5 g of NaCl and 2 g of glucose in 1 liter of water and adjusting the pH to 7.0 with NaOH. The culture (4 ml) was inoculated on 200 ml of MCG medium (0.6% $Na_2HPO_4$, 0.3% $KH_2PO_4$, 0.5% NaCl, 0.1% $NH_4Cl$, 0.5% glucose, 0.5% casamino acid, 1 mM $MgSO_4$, and 4 μg/ml vitamin $B_1$, pH 7.2). After incubating at 30° C. for 4 to 8 hours, 10 μg/ml indolylacrylic acid, which was an inducer of a tryptophan gene, was added to the culture. Incubation was continued for further 2 to 12 hours. The culture was centrifuged at 8,000 rpm for 10 minutes to collect cells, and the cells were washed with 30 mM NaCl and 30 mM Tris-HCl (pH 7.5) buffer. The washed cells were suspended in 20 ml of the aforesaid buffer, and 4 mg of lysozyme and 0.1 ml of 0.25 M EDTA (ethylenediamine-tetraacetic acid) were added to the suspension. After the mixture was allowed to stand at 0° C. for 30 minutes, freezing and thawing were repeated 3 times to disrupt the cells. The mixture was centrifuged at 15,000 rpm for 30 minutes to obtain the supernatant. The supernatant was treated through precipitation with ammonium sulfate, gel filtration with Sephadex G-75, ion exchange chromatography, etc., to obtain about $2 \times 10^6$ units of interferon-γ.

What is claimed is:

1. A method for effecting solubilization of interferon which comprises admixing an amino acid selected from the group consisting of arginine, histidine, lysine, hydroxylysine, ornithine, glutamine, γ-aminobutyric acid, ε-aminocaproic acid and a salt thereof with the interferon.

2. The method according to claim 1, wherein the interferon is selected from the group consisting of interferon-α, interferon-β and interferon-γ.

3. The method according to claim 1, wherein the amino acid is admixed in an amount of $5 \times 10^{-6}$ mole to $5 \times 10^{-3}$ mole per 1,000,000 units of interferon.

4. A composition which contains interferon, albumin, and an amino acid selected from the group consisting of arginine, histidine, lysine, hydroxylysine, ornithine, glutamine, γ-aminobutyric acid, Γ-aminocaproic acid and a salt thereof as a solubilizing agent.

5. The composition according to claim 4, wherein the interferon is selected from the group consisting of interferon-α, interferon-β and interferon-γ.

6. The composition according to claim 4, wherein the amino acid is contained in an amount of 1 mg to 500 mg ($5 \times 10^{-6}$ mole to $5 \times 10^{-3}$ mole) per 1,000,000 units of interferon.

7. The composition according to claim 6, wherein the albumin is contained in an amount of $1 \times 10^{-8}$ mole to $1 \times 10^{-2}$ mole per 1,000,000 units of interferon.

* * * * *